United States Patent
Sasaki et al.

(10) Patent No.: US 11,215,604 B2
(45) Date of Patent: Jan. 4, 2022

(54) METHOD FOR PREDICTING DETERIORATION OF GREASE, GREASE, AND METHOD FOR MANUFACTURING GREASE

(71) Applicant: TOYOTA JIDOSHA KABUSHIKI KAISHA, Toyota (JP)

(72) Inventors: Tomo Sasaki, Toyota (JP); Kazunori Uchiyama, Okazaki (JP); Naoki Hakamada, Anjo (JP); Tadafumi Yoshida, Kasugai (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 290 days.

(21) Appl. No.: 16/284,512

(22) Filed: Feb. 25, 2019

(65) Prior Publication Data
US 2019/0302089 A1    Oct. 3, 2019

(30) Foreign Application Priority Data

Mar. 27, 2018  (JP) .............................. JP2018-060520

(51) Int. Cl.
*G01N 33/28* (2006.01)
*C08J 3/24* (2006.01)
*G01N 33/00* (2006.01)

(52) U.S. Cl.
CPC ............ *G01N 33/2888* (2013.01); *C08J 3/24* (2013.01); *G01N 33/0047* (2013.01)

(58) Field of Classification Search
CPC .... C08J 3/24; G01N 33/0047; G01N 33/2888

USPC .......................................................... 702/34
See application file for complete search history.

(56) References Cited

U.S. PATENT DOCUMENTS

| 3,005,774 A | * | 10/1961 | Shewmaker | ............... | C08J 3/28 |
| | | | | | 508/528 |
| 2016/0208156 A1 | | 7/2016 | Kitazawa et al. | | |

FOREIGN PATENT DOCUMENTS

| JP | 2015-059191 A | 3/2015 |
| JP | 2015-212318 A | 11/2015 |
| JP | 2017-092374 A | 5/2017 |

OTHER PUBLICATIONS ip.com, "Semiconductor device", Murai et al., JP WO2015/102046 A1, Published on Mar. 23, 2017.*

* cited by examiner

*Primary Examiner* — John H Le
(74) *Attorney, Agent, or Firm* — Oliff PLC

(57) ABSTRACT

In a method for predicting deterioration of grease, the grease is applied between a semiconductor module and a cooler. The semiconductor module accommodates a semiconductor element. The method for predicting deterioration includes predicting deterioration of the grease after specified heat cycles by using: a variable G1/G2 that is acquired by dividing an initial storage modulus G1 of the grease by an initial loss modulus G2 of the grease at an expected maximum use temperature of the semiconductor element; and distortion dD of the grease at the time when the initial storage modulus G1 and the initial loss modulus G2 have the same value.

3 Claims, 7 Drawing Sheets

FIG. 5

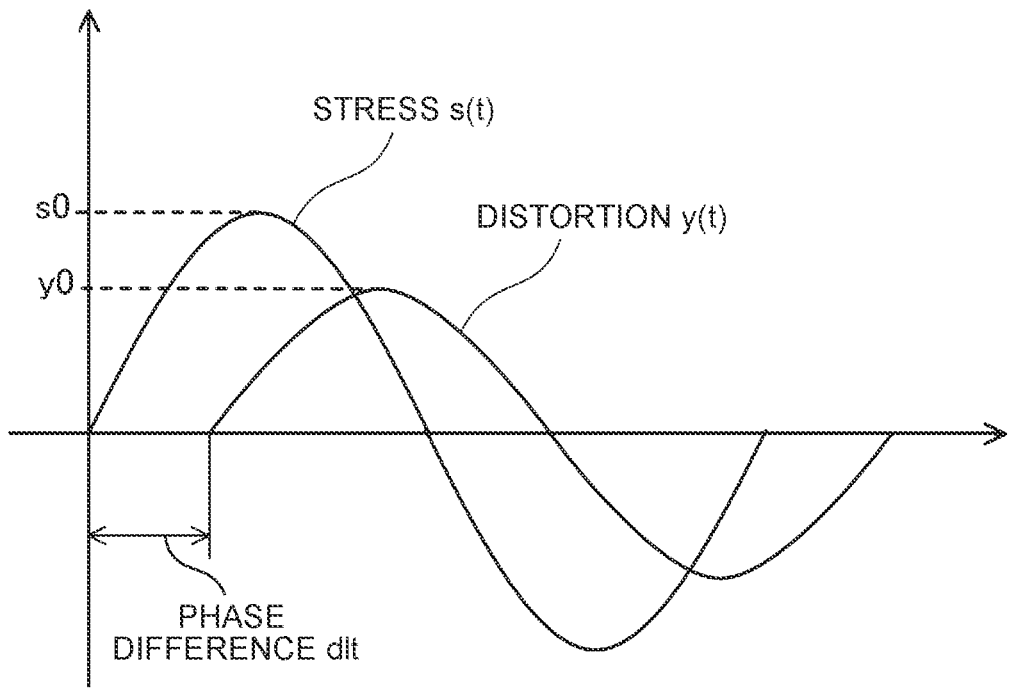

DISTORTION $y(t) = y0 \cdot \exp(i \cdot w \cdot t)$
  STRESS $s(t) = s0 \cdot \exp(i \cdot (w \cdot t + dIt))$ COMPLEX MODULUS $G^* = s(t)/y(t)$
  $= s0 \cdot \exp(i \cdot (w \cdot t + dIt)) / y0 \cdot \exp(i \cdot w \cdot t)$
  $= (s0/y0) \cdot \exp(i\, dIt)$
  $= (s0/y0) \cdot (\cos(dIt) + i \cdot \sin(dIt))$
  $= \underbrace{(s0/y0) \cdot \cos(dIt)}_{\text{STORAGE MODULUS G1}} + i \cdot \underbrace{(s0/y0) \cdot \sin(dIt)}_{\text{LOSS MODULUS G2}}$

RECOVERY : G1/G2

DISTORTION STRENGTH (CROSSOVER DISTORTION) dD:
AMOUNT OF DISTORTION AT RECOVERY G1/G2 = 1

FIG. 8

| | POLYMER SURFACE TENSION (mN/m) | 1-RECOVERY | DISTORTION STRENGTH | INCREASE IN THERMAL RESISTANCE AFTER 200,000 CYCLES | |
|---|---|---|---|---|---|
| | | | | ACTUAL RESULT | PREDICTED VALUE |
| SAMPLE 1 | 22.17 | 0.0523203 | 2.5 | 0.0339 | 0.0338 |
| SAMPLE 2 | 22.43 | 0.0893137 | 35.9 | 0.0164 | 0.0172 |
| SAMPLE 3 | 22.43 | 0.0655098 | 2.6 | 0.037 | 0.0358 |
| SAMPLE 4 | 21.83 | 0.0945977 | 2.7 | 0.046 | 0.0467 |
| SAMPLE 5 | 22.17 | 0.0583895 | 2.7 | 0.0358 | 0.0352 |
| SAMPLE 6 | 21.32 | 0.0587 | 3.3 | 0.0403 | 0.0394 |
| SAMPLE 7 | 22.17 | 0.150999 | 44.2 | 0.0285 | 0.0289 |

METHOD FOR PREDICTING DETERIORATION OF GREASE, GREASE, AND METHOD FOR MANUFACTURING GREASE

INCORPORATION BY REFERENCE

The disclosure of Japanese Patent Application No. 2018-060520 filed on Mar. 27, 2018 including the specification, drawings and abstract is incorporated herein by reference in its entirety.

BACKGROUND

1. Technical Field

A technique disclosed in the present specification relates to a method for predicting deterioration of grease, grease, and a method for manufacturing grease.

2. Description of Related Art

A semiconductor device in which grease is applied between a power card (a semiconductor module), in which a semiconductor element is enclosed, and a heat spreader (a cooler) is disclosed in Japanese Patent Application Publication No. 2017-092374 (JP 2017-092374 A), for example.

When an increase and a decrease in temperature (a heat cycle) of the power card are repeated, out-of-plane deformation of a surface of the power card that opposes the heat spreader repeatedly occurs. When the out-of-plane deformation of the surface of the power card repeatedly occurs, the grease that has been forced out cannot completely return to an original position and is possibly formed with bubbles therein. Such a phenomenon is called "grease leakage". When the grease leakage occurs, heat transfer efficiency from the power card to the heat spreader is decreased. For this reason, the grease, to which the grease leakage is unlikely to occur in the heat cycle, has been demanded. For example, it is disclosed in JP 2015-059191 A that the grease satisfying the following condition exhibits excellent wettability and spreadability and is unlikely to be subjected to the grease leakage.

The condition is as follows. A viscoelasticity measuring equipment capable of measuring shear elasticity is used to measure a storage modulus G1 and a loss modulus G2 of a silicone composition while a temperature of the grease is increased from 25° C. to 125° C. at a rate of 10° C./minute, from 125° C. to 145° C. at a rate of 2° C./minute, and from 145° C. to 150° C. at a rate of 0.5° C./minute and is maintained at 150° C. for 7,200 seconds. In the above case, such a hardened material is produced that the storage modulus G1 after 3,000 seconds from initiation of the temperature maintenance is equal to or lower than 10,000 Pa, that the storage modulus G1 after 7,200 seconds from the initiation of the temperature maintenance is equal to or lower than 100,000 Pa, and that it takes 800 seconds or longer from the initiation of the temperature maintenance for the storage modulus G1 to exceed the loss modulus G2.

SUMMARY

The technique disclosed in JP 2015-059191 A provides the condition of the grease that exhibits the excellent spreadability when the grease is interposed between the power card and the heat spreader and a pressure is applied thereto. In the case where a decrease in the grease leakage is demanded, an initial condition of the grease, which is defined in consideration of performance deterioration of the grease after the specified heat cycles, is preferably acquired in straightforward fashion. In the case where the initial condition of the grease, which is defined in consideration of the performance deterioration, is available, the grease whose deterioration is likely to be insignificant can be selected without performing a deterioration evaluation test instead of performing the evaluation test through trial and error so as to find the grease whose deterioration is likely to be insignificant.

The present specification discloses: a method for predicting performance deterioration of grease applied between a semiconductor module, in which a semiconductor element is accommodated, and a cooler; grease whose performance deterioration over time is likely to be insignificant; and a method for manufacturing such grease.

A first aspect of the disclosure is a method for predicting deterioration of grease. The grease is applied between a semiconductor module and a cooler. The semiconductor module accommodates a semiconductor element. The method for predicting deterioration includes predicting deterioration of the grease after specified heat cycles by using: a variable G1/G2 that is acquired by dividing an initial storage modulus G1 of the grease by an initial loss modulus G2 of the grease at an expected maximum use temperature of the semiconductor element; and distortion dD of the grease at a time when the initial storage modulus G1 and the initial loss modulus G2 have the same value. By adopting a parameter G1/G2 and a parameter dD, the deterioration of the grease can be predicted with a high degree of accuracy. Technical meanings of the parameter G1/G2 and the parameter dD will be described in DETAILED DESCRIPTION OF EMBODIMENTS.

In the method for predicting deterioration, a predicted value A of an increase in thermal resistance of the grease after repeated temperature changes of the semiconductor element from 20° C. to 120° C. for 200,000 cycles is acquired by using Formula 1.

$$A = 0.001 \times (22.57 - 0.7504 \times dD + 267.4312 \times (1 - G1/G2)) \quad \text{(Formula 1)}$$

A second aspect of the disclosure is a method for manufacturing grease. The grease is applied between a semiconductor module and a cooler. The semiconductor module accommodates a semiconductor element. The method for manufacturing includes: a deterioration prediction process; and a filler adjustment process of adjusting a contained amount of a filler based on a result of the deterioration prediction process. The filler is contained in the grease. The deterioration prediction process is a process of predicting deterioration of the grease after specified heat cycles by using: a variable G1/G2 that is acquired by dividing an initial storage modulus G1 of the grease by an initial loss modulus G2 of the grease at an expected maximum use temperature of the semiconductor element; and distortion dD of the grease at a time when the initial storage modulus and the initial loss modulus have the same value.

A third aspect of the disclosure is a method for manufacturing grease. The grease is applied between a semiconductor module and a cooler. The semiconductor module accommodates a semiconductor element. The method for manufacturing includes: a deterioration prediction process; and an adjustment process of adjusting a number of cross-links of crosslinked oil on the basis of a result of the deterioration prediction process. The deterioration prediction process is a process of predicting deterioration of the grease after specified heat cycles by using: a variable G1/G2 that is acquired by dividing an initial storage modulus G1 of the grease by an initial loss modulus G2 of the grease at an expected maximum use temperature of the semiconductor element; and distortion dD of the grease at a time when the initial storage modulus G1 and the initial loss modulus G2 have the same value.

In a fourth aspect of the disclosure, grease is applied between a semiconductor module and a cooler, the semiconductor module accommodating a semiconductor element. In regard to the grease, a variable G1/G2 and distortion dD of the grease satisfy Formula 2. The variable G1/G2 is a variable that is acquired by dividing an initial storage modulus G1 of the grease by an initial loss modulus G2 of the grease at an expected maximum use temperature of the semiconductor element. The distortion dD of the grease is distortion at a time when the initial storage modulus G1 and the initial loss modulus G2 have the same value, satisfy Formula 2.

$$0.02 \geq 0.001 \times (22.57 - 0.7504 \times dD + 267.4312 \times (1 - G1/G2)) \quad \text{(Formula 2)}$$

The grease may further contain silica as a filler.

A fifth aspect of the disclosure is a method for manufacturing grease. The grease is applied between a semiconductor module and a cooler. The semiconductor module accommodates a semiconductor element. In regard to the grease, a variable G1/G2 that is acquired by dividing an initial storage modulus G1 of the grease by an initial loss modulus G2 of the grease at an expected maximum use temperature of the semiconductor element and distortion dD of the grease at a time when the initial storage modulus G1 and the initial loss modulus G2 have the same value satisfy Formula 2. The method for manufacturing includes an adjustment process of adjusting a number of crosslinks of crosslinked oil, $$0.02 \geq 0.001 \times (22.57 - 0.7504 \times dD + 267.4312 \times (1 - G1/G2)) \quad \text{(Formula 2)}.$$

Details of the technique disclosed in the present specification and further improvement therein will be described in "DETAILED DESCRIPTION OF EMBODIMENTS" below.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 5 is a graph for illustrating a storage modulus G1 and a loss modulus G2;

FIG. 8 is a table in which actual values and predicted values of thermal resistance of the grease after 200,000 cycles are compared;

DETAILED DESCRIPTION OF EMBODIMENTS

Figure 1:
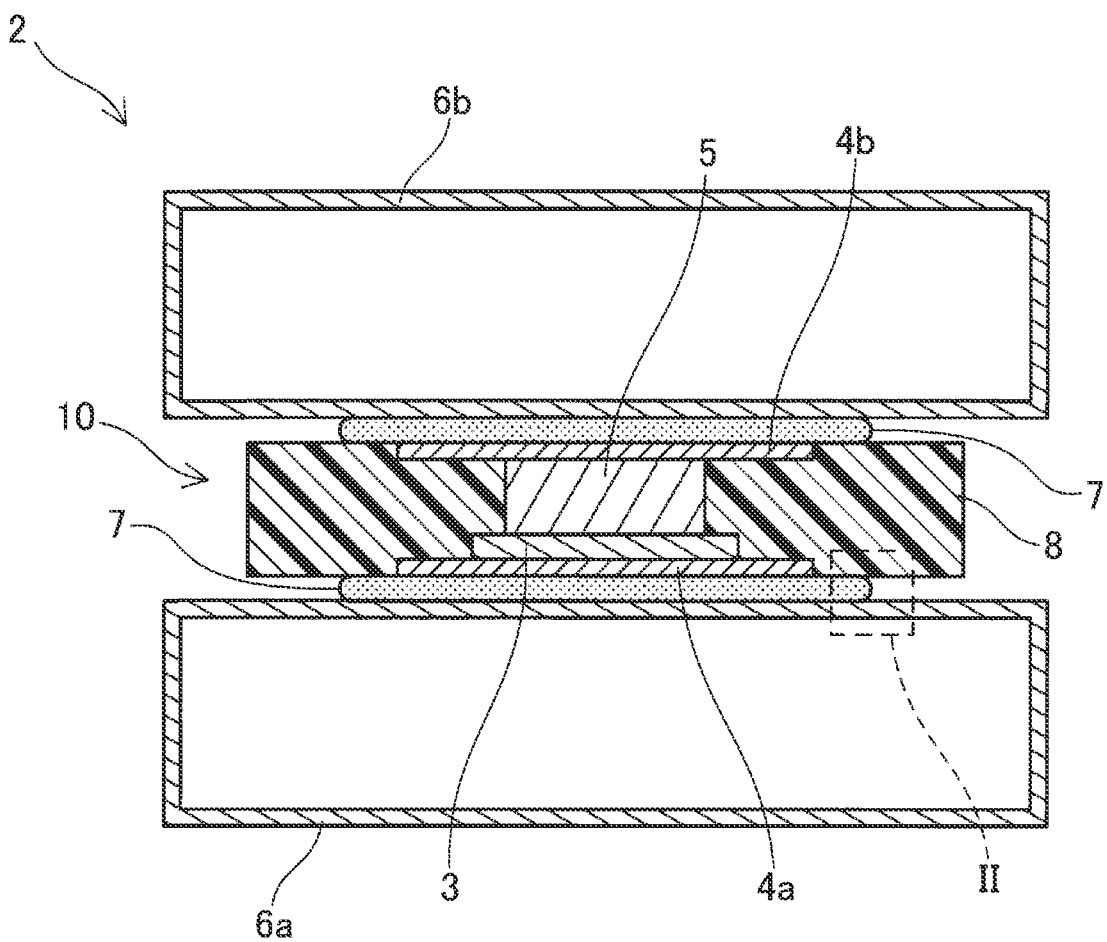
FIG. 1 is a cross-sectional view of a semiconductor device in which a semiconductor module and a cooler are stacked.

A description will be made on a semiconductor device as a target. FIG. 1 is a cross-sectional view of a semiconductor device 2. The semiconductor device 2 includes: a power module 10 (a semiconductor module) having a semiconductor element 3; and a pair of coolers 6a, 6b. The semiconductor element 3 is a power transistor for power conversion. More specifically, the semiconductor element 3 is an insulated-gate bipolar transistor IGBT or a metal-oxide-semiconductor field-effect transistor MOSFET.

A body of the power module 10 is a package 8 that is made of a resin. The semiconductor element 3 and a spacer 5 are enclosed in the package 8. The spacer 5 is made of copper having high electrical conductivity and high thermal conductivity. A cooling wheel 4a is exposed on a surface on one side of the package 8, and a cooling wheel 4b is exposed on the surface on the other side of the package 8. In the package 8, the cooling wheel 4a is joined to a surface on one side of the semiconductor element 3. A collector electrode is exposed on the surface on the one side of the semiconductor element 3, and the cooling wheel 4a is joined to the collector electrode. In the package 8, the cooling wheel 4b is joined to the spacer 5, and an opposite side of the spacer 5 is joined to a surface on the other side of the semiconductor element 3. An emitter electrode is exposed on the surface on the other side of the semiconductor element 3, and the cooling wheel 4b is electrically coupled to the emitter electrode via the spacer 5. Each of the cooling wheels 4a, 4b is thermally coupled to the semiconductor element 3.

The cooler 6a opposes the surface of the power module 10, on which the cooling wheel 4a is exposed, and the cooler 6b opposes the surface of the power module 10, on which the cooling wheel 4b is exposed. Each of the coolers 6a, 6b includes a channel made of aluminum, and a liquid refrigerant flows through the channels. Grease 7 is applied between the cooling wheel 4a of the power module 10 and the cooler 6a, and the grease 7 is also applied between the cooling wheel 4b of the power module 10 and the cooler 6b.

Although not shown, the semiconductor device 2 is pressurized in a stacking direction of the coolers 6a, 6b and the power module 10, and the grease 7 is thinly spread by the applied pressure.

Figure 2:
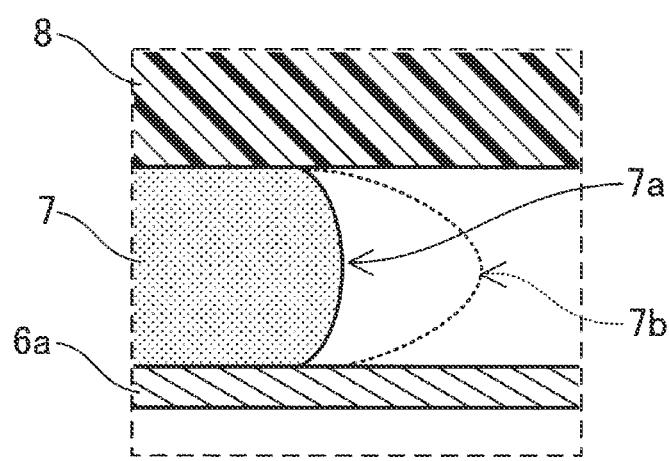
FIG. 2 is an enlarged view of an area of a broken-line rectangular II shown in FIG. 1.

FIG. 2 is an enlarged view of an area of a broken-line rectangular II shown in FIG. 1. In FIG. 2, a portion denoted by a reference numeral and symbol 7a indicates an end of the grease 7 at a normal temperature of the semiconductor element 3. When the temperature of the semiconductor element 3 is increased, out-of-plane deformation occurs to each of the cooling wheels 4a, 4b, and the grease 7 is forced outward. In FIG. 2, a portion denoted by a reference numeral and symbol 7b indicates the end of the grease 7 at the time when the grease 7 is forced outward and moves to a right side. When the semiconductor element 3 is cooled down, and each of the cooling wheels 4a, 4b, to each of which the out-of-plane deformation has occurred, returns to an original shape, the grease 7 returns inward (to a side near the semiconductor element 3). That is, the grease 7 returns to the position denoted by the reference numeral and symbol 7a in FIG. 2. Likelihood of returning to an original shape of the grease 7 depends on a viscoelastic characteristic of the grease 7. When the likelihood of returning to the original shape of the grease 7 is low, bubbles are formed in the grease 7, and heat transfer efficiency from the semiconductor element 3 to the refrigerant in the cooling wheels 4a, 4b is decreased.

Figure 3:
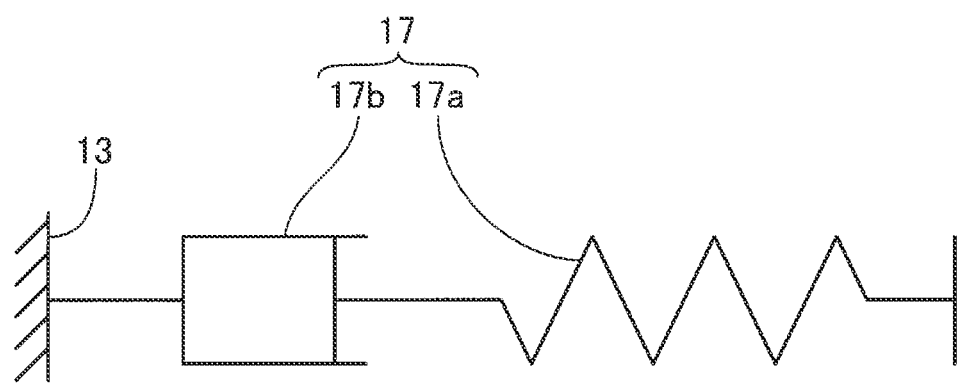
FIG. 3 shows a physical model of grease.

FIG. 3 shows a physical model of the grease. Grease 17 can be modeled by connecting an elastic element 17a and a viscous element 17b in series. A reference numeral 13 denotes a fixed point and corresponds to a center of the grease 7 in FIG. 1. It has been known that a physical characteristic of a viscoelastic body is expressed by a storage modulus G1 and a loss modulus G2. A description will now be made on the storage modulus G1 and the loss modulus G2 of the grease.

Figure 4:
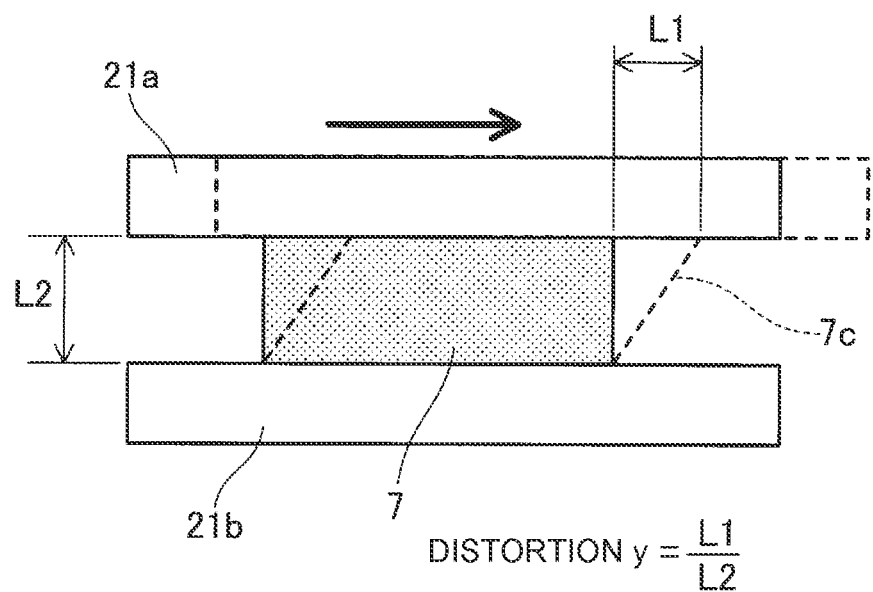
FIG. 4 is a schematic view of an experiment to measure a physical characteristic of the grease.

FIG. 4 is a schematic view of an experiment to measure a physical characteristic of the grease. The grease 7 is sandwiched between two flat plates 21a, 21b, the one flat plate 21b is fixed, and the other flat plate 21a is displaced. When the flat plate 21a moves to a position indicated by a broken line in FIG. 4, the grease 7 is deformed as indicated by a reference numeral and symbol 7c. A thickness of the grease 7 is represented by a symbol L2, and a displacement amount of the end of the grease 7 is represented by a symbol L1. At this time, distortion y of the grease 7 is defined as y=L1/L2. Also, at this time, stress s is generated in the grease 7.

In the model shown in FIG. 4, when the flat plate 21a is periodically vibrated, a phase difference dlt occurs between the distortion y(t) and the stress s(t). FIG. 5 is a graph of the distortion y(t) and the stress s(t), each of which periodically changes. The symbol "w" represents a vibration angular frequency of the flat plate 21a. The symbol "i" represents imaginary number. As shown in FIG. 5, the periodical distortion y(t) and the periodical stress s(t) can be expressed by following Formula 3 and Formula 4, respectively. Note that "dlt" represents a delay (the phase difference) that occurs between the distortion y(t) and the stress s(t).

$$y(t)=y0 \cdot \exp(i \cdot w \cdot t) \quad \text{(Formula 3)}$$

$$s(t)=s0 \cdot \exp(i \cdot (w \cdot t + dlt)) \quad \text{(Formula 4)}$$

As shown in FIG. 5, a complex modulus G* is expressed by following Formula 5.

$$G^*=(s0/y0)\cos(dlt)+i \cdot (s0/y0)\sin(dlt) \quad \text{(Formula 5)}$$

A first term on a right side of Formula 5 corresponds to the storage modulus G, and a second term on the right side corresponds to the loss modulus G2. The storage modulus G1 and the loss modulus G2 are expressed by following Formula 6 and Formula 7.

$$G1=(s0/y0)\times \cos(dlt) \quad \text{(Formula 6)}$$

$$G2=(s0/y0)\times \sin(dlt) \quad \text{(Formula 7)}$$

The storage modulus G1 corresponds to the elastic element 17a in FIG. 3, and the loss modulus G2 corresponds to the viscous element 17b. A variable (G1/G2) acquired by dividing the storage modulus G1 by the loss modulus G2 serves as an index indicating which one of the elastic element and the viscous element exerts greater influence than the other. Here, the variable G1/G2 will be referred to as "recovery".

Figure 6:
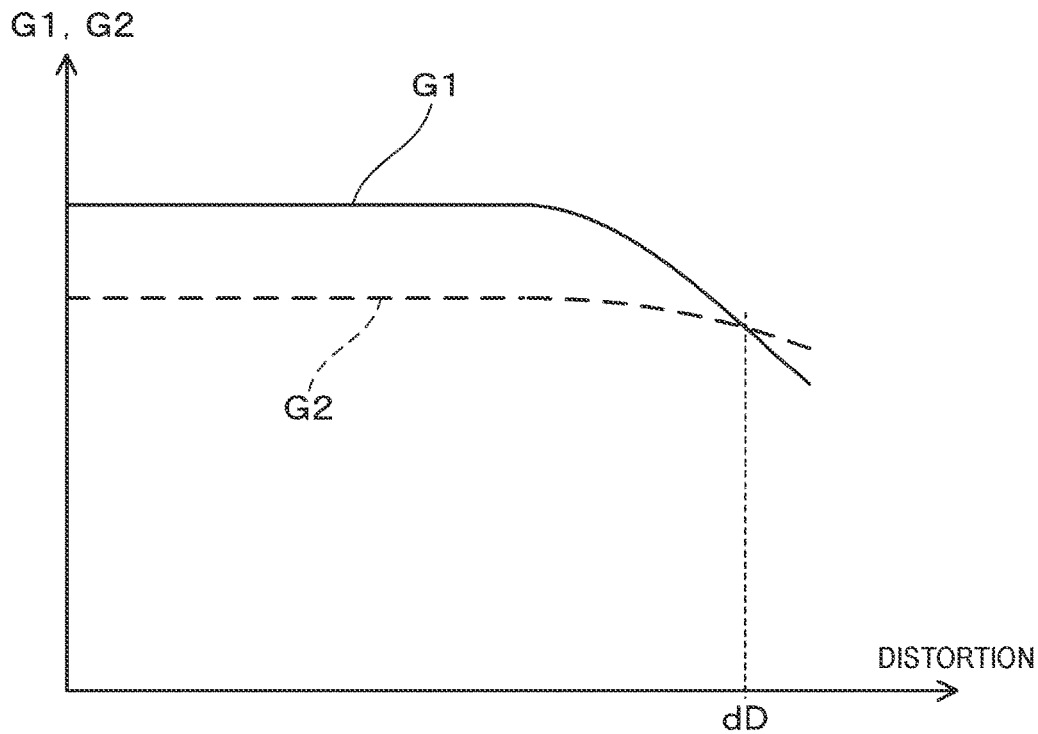
FIG. 6 is a graph for illustrating distortion strength.

In the experiment model shown in FIG. 4, as the flat plate 21a is displaced in one direction, the distortion y=L1/L2 is gradually increased. As the distortion y is increased, the storage modulus G1 and the loss modulus G2 change. FIG. 6 shows the changes in G1 and G2 with respect to the distortion y. Change rates of G1 and G2 with respect to the distortion y differ from each other, and the storage modulus G1 and the loss modulus G2 match each other at specified distortion dD. The distortion dD at this time will be referred to as "distortion strength". The high distortion strength dD means that a recovery force acts well even against the large distortion. As the distortion strength, a value at which G1/G2=1 is satisfied at an expected maximum use temperature (120 [° C.] in this example) of the semiconductor element 3 is adopted. A reason why the value at the expected maximum use temperature of the semiconductor element 3 is used is that a use condition thereof is the most stringent at the expected maximum use temperature. More specifically, a deformation amount of the grease is the largest at the expected maximum use temperature. In this example, deterioration of the grease is predicted by using the storage modulus G1 and the loss modulus G2 at the time.

In order to hinder occurrence of grease leakage (the formation of the bubbles by a heat cycle of the semiconductor element (an out-of-plane deformation cycle of the cooling wheels 4a, 4b)), the grease only needs to have a well-recovered characteristic even with the large distortion. That is, the distortion strength dD may be high, and the recovery G1/G2 may be high. The formation of the bubbles means a decrease in the heat transfer efficiency from the cooling wheel 4a (4b) to the cooler 6a (6b), that is, performance deterioration of the grease. The performance deterioration of the grease appears as an increase in thermal resistance of the grease.

From the consideration so far, the deterioration of the grease after specified heat cycles can be predicted by using: the variable G1/G2 (the recovery) that is acquired by dividing the initial storage modulus G1 of the grease by the initial loss modulus G2 of the grease at the expected maximum use temperature of the semiconductor element 3; and the distortion dD (the distortion strength) of the grease at the time when the initial storage modulus G1 matches the initial loss modulus G2.

The formation of the bubbles results in the decrease in the heat transfer efficiency from the semiconductor element 3 to the coolers 6a, 6b (the refrigerants). The heat transfer efficiency from the semiconductor element 3 to the coolers 6a, 6b (the refrigerants) can be evaluated quantitatively from the thermal resistance. As a result of the earnest investigation, the inventors have found that the deterioration of the grease can be predicted by using the distortion strength dD and the recovery G1/G2 in following Formula 8. A left side A of Formula 8 represents a predicted value (with a unit of ° C./W) of the increase in the thermal resistance of the grease 7 after a temperature change of the semiconductor element 3 from 20° C. to 120° C. is repeated for 200,000 cycles.

$$A=0.001\times(22.57-0.7504\times dD+267.4312\times(1-G1/G2)) \quad \text{(Formula 8)}$$

Here, the initial values of the storage modulus G1 and the loss modulus G2 of the grease are used. The distortion strength dD is also measured on the basis of the initial storage modulus G1 and the initial loss modulus G2 of the grease. The expected maximum use temperature of the semiconductor element 3 herein is 120° C. As shown in FIG. 6, the storage modulus G1 and the loss modulus G2 change along with the change in the distortion. Meanwhile, in the case of FIGS. 1 and 2, the distortion is approximately 10 [%]. Thus, the storage modulus G1 and the loss modulus G2 at the time when the distortion is 10 [%] are used in Formula 8. From the definitions of Formula 6 and Formula 7, G1/G2 is equivalent to tan(dlt).

Figure 7:
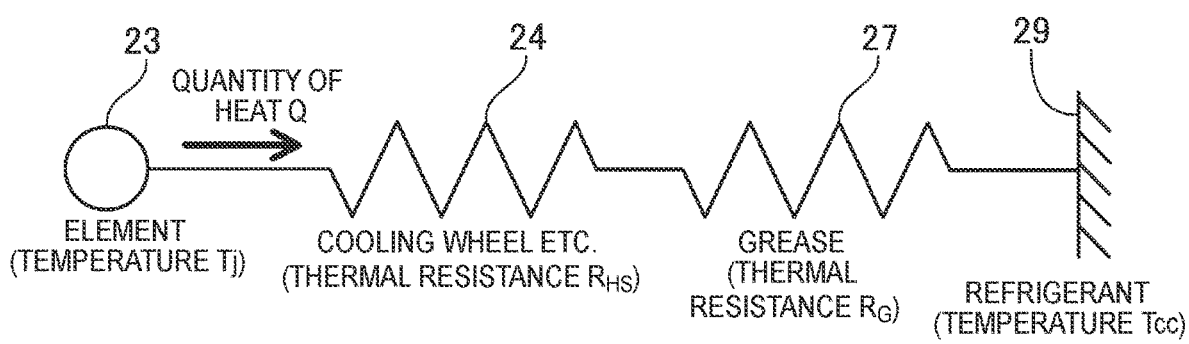
FIG. 7 shows a thermodynamic model of a heat transfer path from a semiconductor element to a refrigerant.

FIG. 7 shows a thermodynamic model of the semiconductor device 2 (FIG. 1) from the semiconductor element 3 to the refrigerant in each of the coolers 6a, 6b. A grease model 27 and another thermal resistance model 24 are interposed between an element model 23 and a refrigerant model 29. The other thermal resistance model 24 includes the cooling wheels 4a, 4b, the spacer 5, casings of the coolers 6a, 6b, and the like. A temperature of the element model 23 is represented by a symbol Tj (an element temperature Tj), and a temperature of the refrigerant model 29 is represented by a symbol Tcc (a refrigerant temperature Tcc). In addition, thermal resistance of the grease model 27 is represented by a symbol $R_G$, and thermal resistance of the other thermal resistance model 24 is represented by a symbol $R_{HS}$. In this case, following Formula 9 is satisfied.

$$(Tj-Tcc)/Q = R_{HS} + R_G \quad \text{(Formula 9)}$$

In Formula 9, a symbol Q represents a quantity of heat generated by the element model 23. When Formula 9 is transformed, following Formula 10 is acquired.

$$R_G = (Tj-Tcc)/Q - R_{HS} \quad \text{(Formula 10)}$$

In one example, the refrigerant temperature Tcc is 65° C., and the thermal resistance $R_{HS}$ of the other thermal resistance model 24 is 0.14 [° C./W]. The quantity of heat Q generated by the element model 23 is 531 [W]. It is understood that, in order to prevent the element temperature Tj from exceeding an allowable temperature limit 150 [° C.], the grease thermal resistance $R_G$ is preferably equal to or lower than 0.02 [° C./W]. In other words, in the case where the grease having the recovery G1/G2 and the distortion strength dD, with which the left side A of Formula 8 is equal to or smaller than 0.02, is selected, there is an extremely high possibility that the temperature of the semiconductor element 3 does not exceed the allowable temperature limit (150° C.) even after the semiconductor element 3 undergoes the above heat cycles (the temperature change from 20° C. to 120° C., 200,000 cycles).

FIG. 8 is a table in which actual values and predicted values of the thermal resistance of the grease 7 after the repeated temperature change of the semiconductor element 3 from 20° C. to 120° C. for 200,000 cycles are compared. As shown in FIG. 8, it is understood that the predicted values acquired by Formula 8 match the actual values well.

According to the investigation by the inventors, it was found that silica having a large surface area was preferably mixed as a filler with the grease so as to make the left side A of Formula 8 fall below 0.02. It was also found that the grease, with which the left side A of Formula 8 fell below 0.02, could be acquired by adjusting (increasing) the number of crosslinks of crosslinked oil during manufacturing of the grease.

Figure 9:
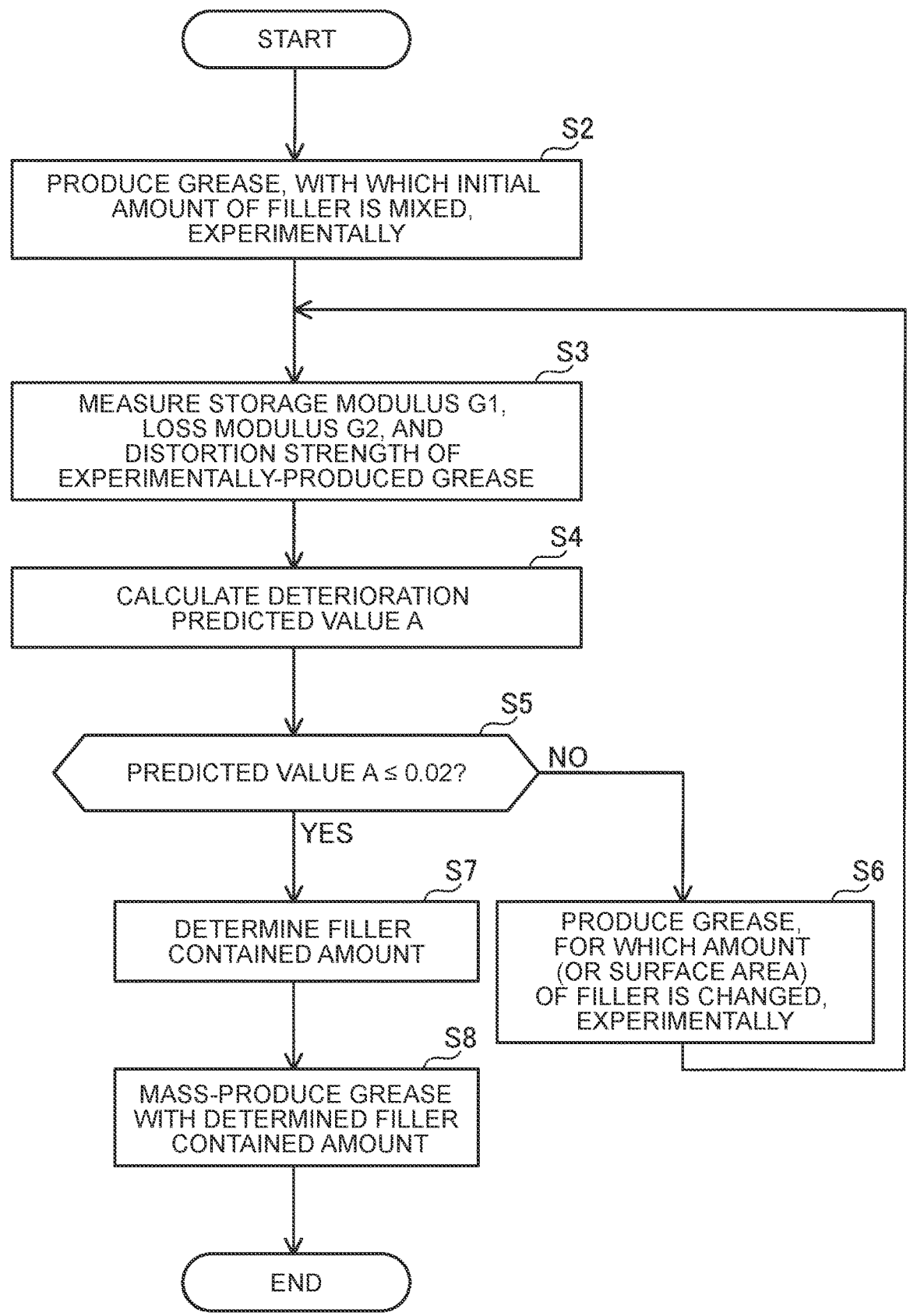
FIG. 9 is a flowchart of a method for manufacturing the grease.

FIG. 9 is a flowchart of a method for manufacturing the grease by using the above method for predicting the deterioration. First, the grease, with which a specified initial amount of the filler is mixed, is produced experimentally (step S2). Next, the initial storage modulus G1, the initial loss modulus G2, and the initial distortion strength dD of the experimentally-produced grease are measured (step S3). Then, the value A (a deterioration predicted value A) of Formula 8 is calculated from the measured values (step S4). If the calculated deterioration predicted value A is not equal to or smaller than 0.02, the grease for which an amount (or the surface area) of the filler is changed is produced experimentally (step S5: NO, S6). Then, the initial storage modulus G1, the initial loss modulus G2, and the initial distortion strength dD of the experimentally-produced grease are measured again (step S3). The value A (the deterioration predicted value A) of Formula 8 is calculated from the measured values (step S4). If the calculated deterioration predicted value A is not equal to or smaller than 0.02, processing in steps S6, S3, and S4 is repeated. If the calculated deterioration predicted value A becomes equal to or smaller than 0.02, a contained amount (and the surface area) of the filler at the time is determined as a design value for mass-production (step S7). Then, the grease is mass-produced with the determined design value (step S8). In this way, the grease, whose deterioration of the heat transfer efficiency is insignificant, can be mass-produced. The insignificant deterioration of the heat transfer efficiency means that the increase in the thermal resistance of the grease is insignificant so as to prevent the temperature of the semiconductor element from exceeding the allowable temperature limit even after the specified heat cycles.

Note that the adjustment of the amount of the filler and the adjustment of the surface area of the single filler exert the same effect. This is because both of those adjustments are equivalent to the adjustment of the surface areas of all the fillers. Steps S3 and S4 correspond to a process of predicting the deterioration by using the method for predicting the deterioration. Steps S5 and S6 correspond to a filler adjustment process of adjusting the amount of the filler contained in the grease on the basis of the result of the deterioration prediction.

Figure 10:
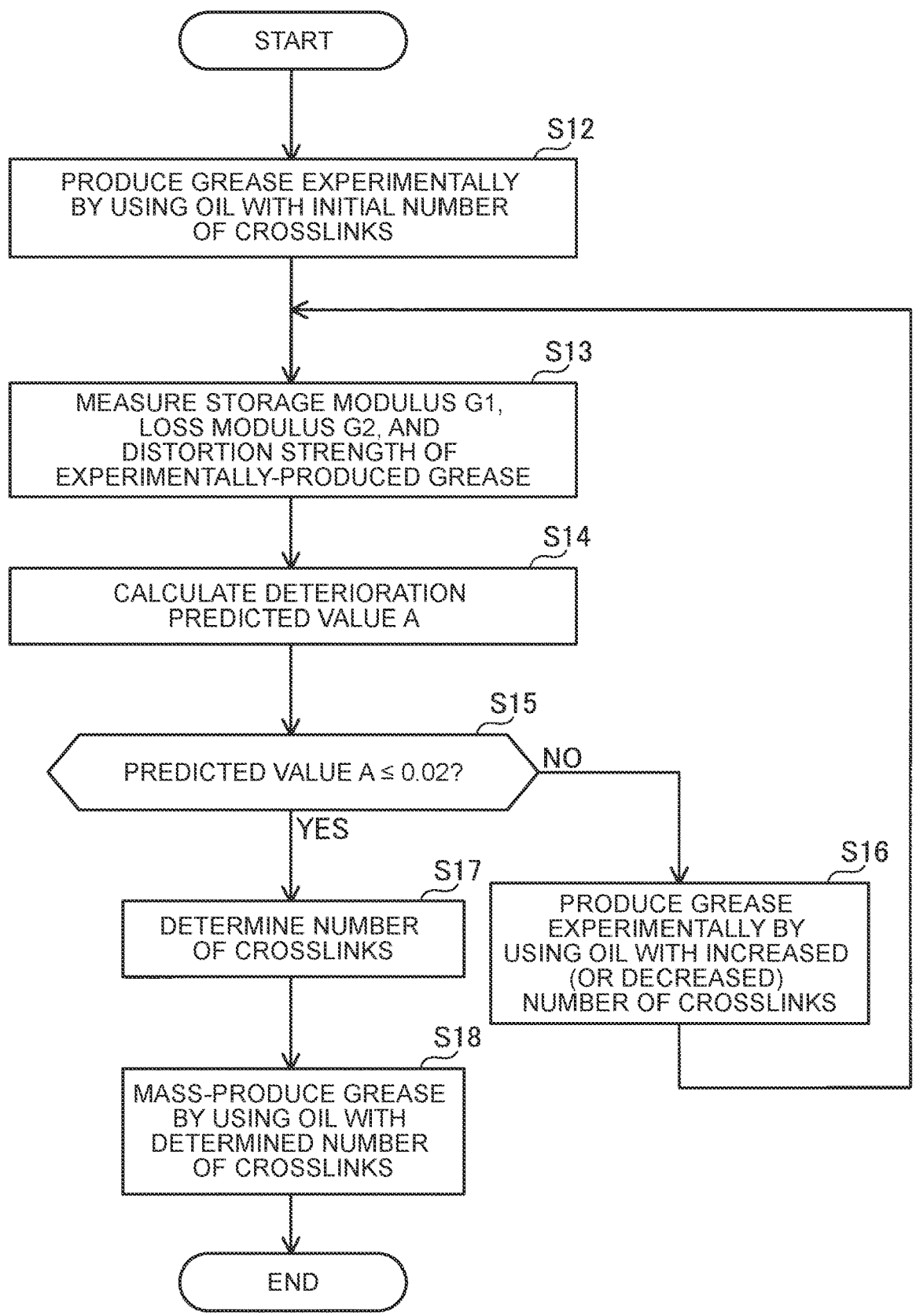
FIG. 10 is a flowchart of another method for manufacturing the grease.

FIG. 10 is a flowchart of another method for manufacturing the grease by using the above method for predicting the deterioration. First, the grease, for which the oil with the specified number of the crosslinks is used, is produced experimentally (step S12). Next, the initial storage modulus G1, the initial loss modulus G2, and the initial distortion strength dD of the experimentally-produced grease are measured (step S13). Then, the value A (the deterioration predicted value A) of Formula 8 is calculated from the measured values (step S14). If the calculated deterioration predicted value A is not equal to or smaller than 0.02, the grease is produced experimentally by using the oil with the increased (or decreased) number of the crosslinks (step S15: NO, S16). Then, the initial storage modulus G1, the initial loss modulus G2, and the initial distortion strength dD of the experimentally-produced grease are measured again (step S13). The value A (the deterioration predicted value A) of Formula 8 is calculated from the measured values (step S14). If the calculated deterioration predicted value A is not equal to or smaller than 0.02, processing in steps S16, S13, and S14 is repeated. If the calculated deterioration predicted value A becomes equal to or smaller than 0.02, the number of the crosslinks at the time is determined as the design value for the mass-production (step S17). Then, the grease is mass-produced with the determined design value (step S18). In this way, the grease, whose deterioration of the heat transfer efficiency is insignificant, can be mass-produced. The insignificant deterioration of the heat transfer efficiency means that the increase in the thermal resistance of the grease is insignificant so as to prevent the temperature of the semiconductor element from exceeding the allowable temperature limit even after the specified heat cycles.

Steps S13 and S14 correspond to the process of predicting the deterioration by using the method for predicting the deterioration. Steps S15 and S16 correspond to the filler adjustment process of adjusting the amount of the filler contained in the grease on the basis of the result of the deterioration prediction.

The specific examples of the disclosure have been described so far in detail. However, the specific examples are merely illustrative and do not limit the claims. The technique described in the claims includes various modifications and changes that are made to the specific examples described so far. The technical elements that are described in the present specification and the drawings demonstrate technical utility when used singly or in various combinations, and thus are not limited to the combinations described in the claims in the original application. In addition, the techniques that are described in the present specification and the drawings achieve a plurality of objects simultaneously, and the achievement of one object thereof itself has technical utility.

What is claimed is:

1. A method for manufacturing grease,
the grease being applied between a semiconductor module and a cooler, and the semiconductor module accommodating a semiconductor element,
the method for manufacturing the grease comprising:
producing an experimental grease using a crosslinked oil with a specified number of crosslinks;
measuring an initial storage modulus G1, an initial loss modulus G2, and a distortion dD of the experimental grease, the distortion dD being a value at a time when the initial storage modulus G1 and the initial loss modulus G2 have the same value,
performing a deterioration prediction process that is a process of predicting deterioration of the experimental grease by using a variable G1/G2 that is acquired by dividing the initial storage modulus G1 by the initial loss modulus G2 at an expected maximum use temperature of the semiconductor element and the distortion dD;
performing an adjustment process of adjusting the number of the crosslinks of the crosslinked oil based on a result of the deterioration prediction process;
determining the number of the crosslinks adjusted in the adjustment process as a design value for a mass-production; and
mass-producing the grease with the determined design value.

2. The method for manufacturing the grease according to claim 1, wherein the variable G1/G2 and the distortion dD satisfy the following Formula 2, $$0.02 \geq 0.001 \times (22.57 - 0.7504 \times dD + 267.4312 \times (1 - G1/G2)) \quad \text{(Formula 2)}.$$

3. The method for manufacturing the grease according to claim 1, wherein:
a predicted value A of an increase in thermal resistance of the grease after a temperature change of the semiconductor element from 20° C. to 120° C. is repeated for 200,000 cycles by using the following Formula 1; and
in a case where the predicted value A is not below 0.02, the number of the crosslinks of the crosslinked oil is adjusted by increasing the number of the crosslinks of the crosslinked oil, $$A = 0.001 \times (22.57 - 0.7504 \times dD + 267.4312 \times (1 - G1/G2)) \quad \text{(Formula 1)}.$$

* * * * *